United States Patent [19]

Egolf

[11] Patent Number: 4,744,791
[45] Date of Patent: May 17, 1988

[54] SYRINGE WITH AUTOMATIC PISTON RETRACTION

[76] Inventor: Georges Egolf, 1933 Prospect Street, Sherbrooke, Canada, J1J 4C9

[21] Appl. No.: 946,498

[22] Filed: Dec. 18, 1986

[51] Int. Cl.$^4$ ............................................. A61M 5/315
[52] U.S. Cl. ..................... 604/229; 604/168; 604/900; 604/220
[58] Field of Search ............... 604/229, 220, 900, 168, 604/218; 128/765

[56] References Cited

U.S. PATENT DOCUMENTS

| | | | |
|---|---|---|---|
| 2,526,365 | 10/1950 | Jorgensen | 604/229 |
| 3,307,548 | 3/1967 | Kachergis | 604/220 |
| 3,583,399 | 6/1971 | Ritsky | 604/900 |
| 3,618,603 | 11/1971 | Levenson | 604/229 |
| 3,669,111 | 6/1972 | Dubner | 604/229 |
| 4,333,458 | 6/1982 | Margulies et al. | 604/220 |
| 4,518,385 | 5/1985 | Lindmayer et al. | 604/414 |

*Primary Examiner*—C. Fred Rosenbaum
*Assistant Examiner*—Denise Whelton

[57] ABSTRACT

The syringe is of the aspirating type and comprises a transparent barrel, having an outlet spout for mounting a hypodermic needle at one end and fully open at its opposite end. A partition separates the barrel into a shorter and a longer chamber, the latter for containing the liquid to be injected. A plunger assembly has a piston rod slidable through the partition. A rubber sleeve, surrounded by a casing, is frictionally, slidably mounted on the piston rod in the shorter chamber, and a compression coil spring freely surrounds the piston rod between the casing and the partition. A lever plate is pivotable on one of the fingergrips of the barrel between an open position and a closed position, trapping the sleeve, the casing and the spring into the shorter chamber with the spring in compressed condition. Opening of the lever plate immediately before injection automatically induces partial retraction of the plunger assembly. Any release of the pushing pressure on the plunger during injection also allows the coil spring to partially retract the plunger.

9 Claims, 2 Drawing Sheets

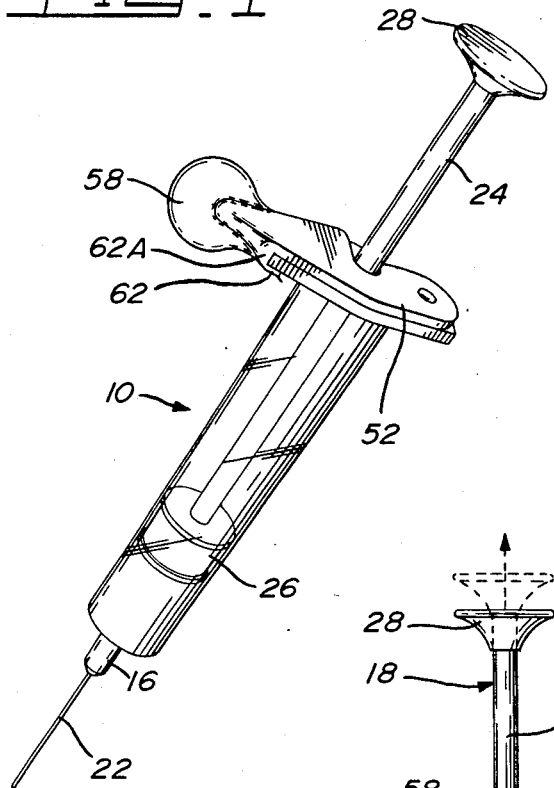
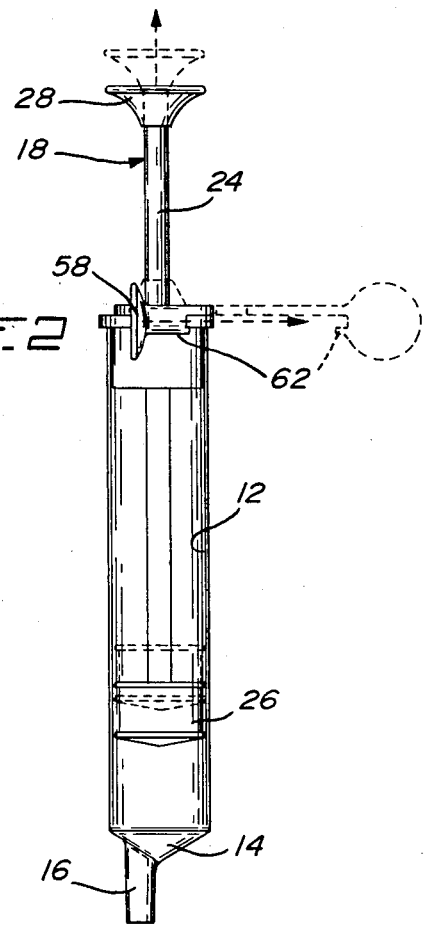
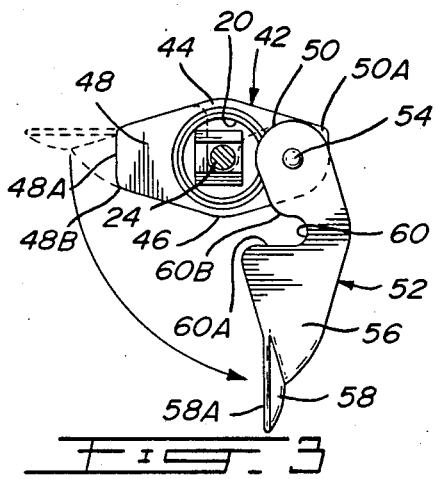

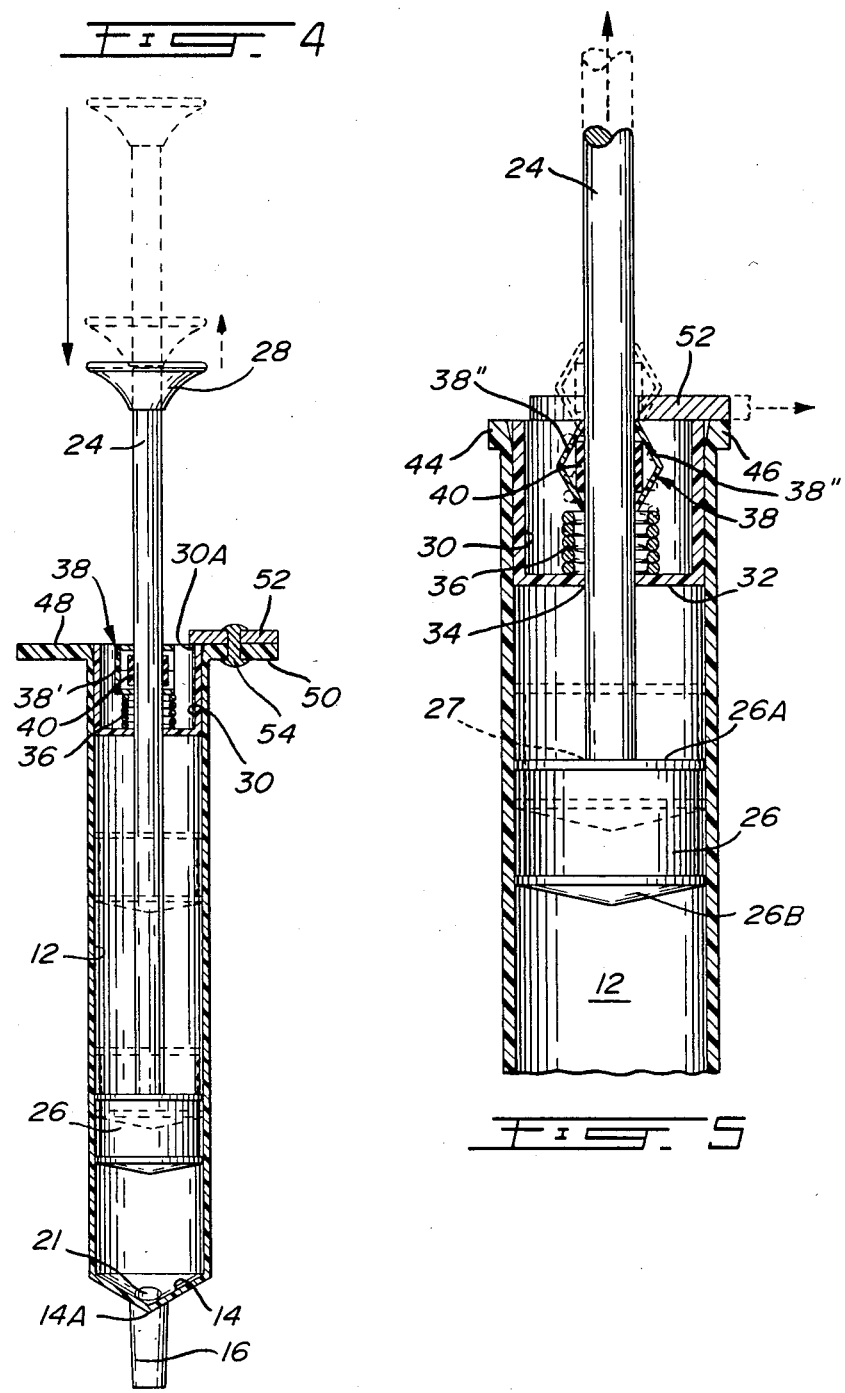

SYRINGE WITH AUTOMATIC PISTON RETRACTION

FIELD OF THE INVENTION

This invention relates to syringes for medical use, including dental and veterinary uses, and more specifically, to an automatic safety mechanism which will enable a health officer to regularly verify during the injection of a fluid in vivo that the syringe needle remains within the blood vessel and not elsewhere.

BACKGROUND OF THE INVENTION

It has been a recent trend in Courts of Justice of the industrial world, and more particularly in the United States, to award in medical malpractice cases increasing monetary compensations, which now reach huge amounts. In the United States, for example, several of such monetary compensations are now well in excess of one million dollars per patient; costs of medical liability insurance have accordignly soared, and in certain medical specialties, the yearly premiums almost reach $100,000 (U.S.): this is about five times the Gross National Product per capita of the United States (in 1986); of course, health care fees have increased accordingly, but it is the consumer-patient who ultimately loses on the long run.

Among the doctors in medicine most susceptible of malpractice suits, there are inter alia the anesthesists. One frequent medical act effected by anesthesists is the injection of anesthetic solutions in the blood vessel of a patient. When the patient is to be fully anesthesized, as for a major operation, the anesthesist has to inject the anesthetic solution both before the operation, and during the operation to continuously provide for an adequate level of neuro-muscular release of the patient. This is done with a syringe, and it is always a delicate operation to not only >>find<< the blood vessel with the syringe needle, especially with patients suffering from obesity wherein the blood vessels are embedded in large masses of fat, but also prevent its withdrawal therefrom notwithstanding the inevitable play of the needle in the tissues both during the injection and in between injections when the needle is normally not removed from tissues as during general anesthesy for a major surgical operation.

Of course, physically-damaging consequences to the patient may result from inadequate use of a syringe: for example, abscesses and cutaneous fistules.

There are two main types of syringes: the >>glass<< type and the disposable, single-use type. In the former, often used by anesthesists, means may be provided for regularly verifying if the needle is still in the blood vessel; such means are disclosed in French Pat. No. 7 615 801, issued Feb. 20, 1981 to the present inventor. However, there is a danger that multiple-use type of syringes, such as the glass syringes, may induce once in a while imperfect sterilization of the syringe, and therefore risks of contamination. It is known, for example, that certain strains and viruses can survive for long times on dry substrates and resist against at least some of the sterilization method presently used. In the last few years, the virus of a dangerous and devastatingly-deadly disease has spread over the world, to wit: the AIDS disease. Also, human error and sterilizating machine dysfunction do occur. In view thereof, it is the present inventor's firm belief that the use of non-disposable types of syringe should be completely banned in the future.

Conventional disposable syringes, made of polypropylene, do not have such safety means for regularly automatically verifying if the needle is in the vein. During injection with disposable syringes by health officers, such a safety operation is effected by partially pulling out the syringe piston from the syringe tubular body; if blood backflows into the transparent syringe tubular body, as witnessed de visu by a reddish stream of fluid, then the needle must necessarily be in the blood vessel. This is well known in the art. However, this requires the two hands of the health officer; one for holding the syringe, and one for pulling back the piston centrally with the fluid-ejecting operation, then the health officer may single-handedly support the syringe main body with two or three fingers of one hand and push the piston with the thumb of the same hand.

That two hands are required for verifying that the needle is within a blood vessel is inefficient, time-consuming, and inevitably undesirably induces some play of the needle in the surrounding tissues.

It is also known that piston pull-back in a disposable or one-use syringe requires more effort than in a glass syringe, since the former requires sealing rings around the piston head and these rings produce friction.

SUMMARY OF THE INVENTION

The present invention is an improvement over the above-mentioned French patent. There is accordingly disclosed a syringe for medical purposes comprising: a main transparent cylindrical tube, designed to contain a fluid and having a top mouth and a narrowed bottom outlet spout, the spout adapted to be mounted by a needle, the needle to engage a blood vessel. A partition is fixedly mounted within said tube, a short distance from said mouth and defining a central bore. The partition divides the tube in two chambers, namely: a shorter top chamber and a longer bottom chamber. A plunger is provided, including a cylindrical piston rod slidingly engaged through said partition bore, with a pusher head at its outer end and a cylindrical plug at its inner end, said plug sealingly, slidingly engaging the interior face of said lower chamber An elastic sleeve is frictionally slidably mounted to said piston rod upstream from said partition. The sleeve can slide on the piston rod in either direction. A casing surrounds said elastic sleeve and is freely slidable on the piston rod. A biasing member is freely slidably mounted to said piston rod between said casing and said partition, and abuttable against said elastic sleeve. Releasable lock means trap said elastic sleeve into said tube top chamber against the bias of said biasing member.

Release of said lock means immediately before injection of said fluid in the blood vessel automatically induces partial retraction of the piston rod from said main tube. During injection, the elastic sleeve allows piston rod movement but biases the biasing member. Any release of the pushing pressure on the piston head during injection allows said biasing member to partially retract said piston from said main tube. Each of said partial retractions of the piston from the main tube is adapted to generate a back-flow of virtually-detectable red-dish blood stream into said transparent main tube, when the tip of the needle is well within said blood vessel.

BRIEF DESCRIPTION OF THE DRAWINGS

FIG. 1 is a perspective view of a preferred embodiment of the syringe according to the invention, being in its condition prior to fluid-ejection and controlled by a hand-illustrated in dotted lines;

FIG. 2 is an elevation of the syringe, shown in its condition prior to fluid-ejection in full lines and in its fluid-ejecting condition in dotted lines;

FIG. 3 is a top end view of the syringe, shown in its fluid-ejecting condition in full lines and in its condition prior to fluid-ejection in dotted lines;

FIG. 4 is a sectional elevation of the syringe, at a slightly-enlarged scale relative to FIG. 2, and illustrating the slight upward retraction of its piston upon release of the pushing force of the operator's thumb on the piston head, accordingly with a first feature of the invention; and FIG. 5 is a fragmentary sectional elevation of the syringe, taken at right anglesto FIG. 4, and illustrating the lever plate in closed position to compress the coil spring, whereby automatic retraction of the piston will take place upon opening movement of the lever plate.

DETAILED DESCRIPTION OF THE PREFERRED EMBODIMENT OF THE INVENTION

Disposable syringe 10 conventionally consists of a large cylindrical hollow tube or barrel 12, tapered at its lower outlet end 14 to form a funnel-shaped portion, and from which projects a diametrally-smaller bottom cylindrical spout 16, the large tube 12 being fitted with a plunger 18 slidingly engaged thereto. Bottom spout 16 opens into tube 12 through a bore 21 (FIG. 4) and is designed to be fitted with a metallic needle 22.

According to specific features of the syringe, the large tube 12 is made of a transparent plastic material, for instance polypropylene, whereby the syringe 10, including piston 18 and needle 22, is of the disposable single-use type. As best shown in FIG. 2, bottom spout 16 is axially offset (excentric) from the central longitudinal axis of large tube 12, but is within the plane passing through both this latter axis and the apex 14A of the funnel-shaped bottom end 14, see FIG. 4. Moreover, this central longitudinal axis of tube 12 passes through the apex 14A of the tapered end 14.

Plunger 18 includes a long diametrally thin cylindrical piston rod 24, being non cross-sectionally X-shaped contrarily to conventional piston rods, and being provided at one end with a plastic plug 26 engaging into the tube 12, and at the other end with an enlarged flat pusher head or thumb plate 28. Rod 24 and head 28 may be made of cheap plastic material, which need not be necessarily transparent.

More particularly, plug 26 is axially bored in its center, at bore 27, for engagement by rod 24. Two sealing rings 26A, 26B are spacedly secured to plug 26. The lower end of plug 26 is conical to abut against and conform to the shape of lower funnel-shaped tube end 14 when piston 18 reaches its bottom limit position; rod 24 is conventionally longer than tube 12, whereby head 28 always remains above the top mouth 20 of tube 12. Rings 26A, 26B are diametrally slightly greater than plug 26, so that when piston rod 24 moves along tube 12, it is the peripheral edges of rings 26A, 26B which will frictionally (sealingly) slide along the interior face of tube 12, the peripheral surface of plug 26 being slightly spaced therefrom.

Two further elements are provided at the upper portion of tube 12, and best shown in FIGS. 4–5 of the drawings. The first of such elements consists of a cylinder body 30, having an open top end 30A and a closed bottom floor or partition 32, and frictionally lockingly secured by a friction-fit to the inside of the upper portion of tube 12. Bottom partition 32 of body 30 is flat and includes a central through-bore 34 through which is slidably engaged piston rod 24. Body 30 may be made of transparent plastic material. The top limit position of plunger 18 is thus defined when the top disk 26A of plug 26 flatly abuts against flat partition 32 of body 30.

A compression coil spring 36 is freely mounted to piston rod 24, upstream of partition 32. A casing 38, made of a plastic material, is freely slidably mounted to piston rod 24, for up-and-down movement therealong between coil spring 36 and piston head 28. A sleeve 40, made of a silicone-rubber elastic material, is frictionally slidably mounted to piston rod 24, for up-and-down movement relative to piston rod 24. Sleeve 40 exerts a constant friction on piston rod 24 in either direction. Sleeve 40 is surrounded by casing 38; casing 38 has registering top and bottom bores for slidable engagement by rod 24, and an opened side, (see FIG. 4) for insertion of sleeve 40 within casing 31 prior to fitting the resulting assembly on the piston rod 24. Once sleeve 40 and casing 48 are fitted on piston rod 24, plug 26 is fixed to piston rod 24. Casing 38 is shown with a straight side wall 38' opposite its open side in FIG. 4, and two angular side walls 38" normal to the straight side wall 38' (see FIG. 5). However, the specific shape of casing 38 is not important. This casing provides two abutment members at the two ends of sleeve 40. An assembly similar to spring 36, plastic casing 38 and silicone rubber sleeve 40 is already disclosed in relation to a syringe, in French Pat. No. 7 615 801, issued Feb. 20, 1981 to the present inventor (see FIG. 7 more particularly); accordingly, they do not per se constitute the subject matter of the present invention and, thus, need not be further described. Let us only say that, for the sake of clarity, when piston 18 is substantially vertical and is pushed into tube 12, coil spring 36 slides freely on piston rod 24 and abuts against partition 32, the piston rod carrying therewith elastic sleeve 40 and casing 38, until casing 38 comes to abut against coil spring 36; then, as clearly shown by the vertical arrows in FIG. 4, the latter spring 36 is compressed by elements 38-40 up to a maximum level, beyond which piston rod 18 will further slide through elements 38-40 as well since the pressure exerted by the user on head 28 is sufficient to overcome the friction of sleeve 40 on piston rod 24; thereafter, it is readily understood that any release of the pushing pressure on the piston head 28 will allow the coil spring 36 to express its bias, thereby upwardly pushing on casing 38 which forces sleeve 40 to retract piston rod 18; thus, the piston automatically upwardly retracts for a short distance. Hence, when injecting a fluid into a blood vessel, the simple release of pressure on the piston head 28 will automatically retract the piston, so that, if a small stream of (reddish) blood back flows into the transparent tube 12, the physician can immediately obtain a de visu confirmation that he is in the blood vessel and not (undesirably) elsewhere in the tissues.

The top circular edge of cylindrical body 12 conventionally includes an outturned flange 42, best shown in FIG. 3. On two opposite first sides of tube 12, the flange portions are thin, at 44, 46; on the other two sides, the flang portions are much larger at 48, 50, each of the latter portions defining outwardly-converging side edges and an outermost edge 48A, 50A, which is slightly smaller than the diameter of tube 12. Flanges 48, 50 are designed to constitute finger grips for the fingers of the physician's hand H when his thumb pushes the thumb plate 28 of the plunger 18.

A rigid, elongated lever plate 52 is pivotally mounted at one end to flange portion 50 by a rivet 54. Plate 52 may be made of a rigid plastic or metallic alloy material. Plate 52 (FIG. 3) includes a main flat surface 56, adapted to slide against the top face of flange 42 during its pivotal action about rivet 54. Plate 52 is longer than flange 42 and includes at its free end a substantially-circular tab projection 58 in a plane at right angles to that of main face 56. Tab 58 includes a concave face 58A on one side for contact by a finger F of a physician or health officer for pivoting plate 52 to an open position. Plate 52 includes an intermediate notch 60 on the same side as the tab face 58A, notch 60 defining a radially-outward edge 60A, which is about twice as long as the radially-inward edge 60B. Rod 24 transversely engages notch 60 when lever plate 52 is pivoted to a closed position where it completely overlies flange 42 (see FIGS. 1-2).

In this latter closed position of the lever plate 52, its registering portion substantially conforms to the shape of flange 42. A downturned border 62 is also provided to the free end portion plate 52, proximate tab 58, and forming a slightly-inwardly-extending flange, which is on the side opposite that of face 58A. This downturned border 62 is adapted to slide against the underface of flange edge portion 48A, when the plate 52 moves to its closed position, also to abut at its trailing end 62A against the adjacent side wall corner 48B of that flange portion 48, to prevent further pivotal action thereof. Border 62 and plate 52 have a friction-fit with flange portion 48 to prevent accidental opening movement. When in closed position, lever plate 52 forms a seat for casing 38, and the distance between plate 52 and partition 32 is about equal to the sum of the lengths of the fully-compressed coiled spring 36 and of casing 38. When piston 18 is pushed into tube 12, casing 38 and sleeve 40 move wih the piston rod 24 and, finally, fully compress coil spring 36, and then piston rod 24 slides through elements 36, 38, 40. In this condition, elements 36, 38, 40 are all below the pivotal plane of lever plate 52, whereby the latter can be pivoted to its closed position, trapping elements 36, 38, 40, with coil spring 36 in its fully-compressed condition.

Supposing the syringe 10 is full of liquid with locking plate 52 in closed position, the user inserts the needle into the blood vessel and then pushes with his finger on tap 58 to open lever plate 52. This causes release of coil spring 36 and retraction of the piston. This automatic piston retraction is therefore effected immediately before syringe is used in ejecting a liquid (see the arrows of FIG. 5). This allows a physician to single-handedly and conveniently check if the needle is really into the blood vessel, i.e. with the same hand that supports the syringe 10 and before liquid injection takes place.

The user then starts the injection, during which lever plate 52 remains in open condition. Anytime during injection, he can release pusher head 28 and automatic piston retraction takes place, again constituting a check that the needle is still in the blood vessel.

To avoid air entry into the syringe during filling of the latter with the treating liquid, lever plate 52 is kept in closed position.

The piston 18 may be advantageously constructed in either one of the following manners: rod 24 may have male threads at both ends and head 28 may have female threads in a cavity mounted centrally thereof, and plug 26 has a central threaded bore, wherein head 28 and plug 26 would be screwed to rod 24; or the threads of elements 24, 26, 28 could be cancelled, whereby elements 24, 26, 26, 28 would then be mounted to rod 24 by friction-fit; or head 28 and rod 24 could be integrally molded.

Border 62 constitutes guide means for the final leg of the pivotal movement of the rigid lever plate 52, being exactly parallel to the mouth flange 42.

In addition to the fact that the syringe of the invention provides means to verify that the needle is properly positioned both before and during injection, it has the following advantages: during injection, silicone rubber sleeve opposes a resisting force to the injecting movement of the piston and this prevents the user from injecting at too fast a rate, thus preventing pain to the patient.

The closed position of the lever plate 52 serves as a visual clue to the user that the syringe has never been used. For instance, the user, after having removed the wrapping of a new-disposable syringe, preparatory to make an injection, may be called away from the patient for a certain time; prior to leaving, he deposits the unsheathed syringe on a sterile pad. Upon his return to the patient, he will see that the syringe has its lever plate 52 in closed position, and this will give him the assurance that the syringe has never been used.

What I claim is:

1. An aspirating hypodermic syringe comprising a barrel having at one end a spout for mounting a needle and at the opposite end a fully-open mouth; a partition fixed within said barrel nearer said mouth than said spout and defining a longer chamber between said partition and said spout, and a shorter chamber between said partition and said mouth, said partition having a bore therethrough; an outwardly-projecting flange at said opposite end defining finger grips; a plunger including a piston located in said longer chamber, a piston rod fixed to said piston and extending through said bore of said partition, through said shorter chamber and beyond said opposite end of said barrel and terminated by a thumb piece fixed thereto; a sleeve frictionally surrounding said piston rod and slidable thereon in either direction, said sleeve located between said partition and said thumb piece; a biasing member freely surrounding said piston rod between said sleeve and said partition; the assembly of said sleeve and biasing member having a first position completely located in said shorter chamber with said biasing member abutting said partition and in biased condition, and having a second position partially projecting beyond said shorter chamber past said mouth when said biasing member is in unbiased condition, the friction force exerted by said sleeve on said piston rod and the retraction force exerted by said biasing member on said sleeve being sufficient to partially retract said plunger from said barrel away from said spout, a pushing force exerted by a user on said thumb piece to advance the piston towards said spout capable of overcoming the resistance of said sleeve and of biasing said biasing member; and further including a manually-operated abutment member mounted on said flange and movable between a closed position closing said mouth and trapping said assembly in said first position, and an open position releasing said assembly, so that said biasing member is allowed to cause said partial retraction of said plunger.

2. A syringe as defined in claim 1, wherein said partition is provided with a cylindrical skirt and the assembly of said partition and of said skirt is mounted within said barrel at said mouth, with a friction-fit.

3. A syringe as defined in claim 1, wherein said barrel is of transparent material and said syringe is of the disposable single-use type.

4. A syringe as defined in claim 1, wherein said biasing member is a compression coil spring.

5. A syringe as defined in claim 4, wherein said abutment member is an elongated lever plate pivoted by a pivot member on said flange about an axis substantially parallel to that of said barrel and provided with a lateral notch partially surrounding said piston rod in the closed position of said abutment member, to allow advancing and retracting movement of said piston rod even when said abutment member is in closed position.

6. A syringe as claimed in claim 5, wherein said flange includes two oppositely-directed flange portions to define two transversely-opposite finger grips, said lever plate being pivoted to one of said flange portions, conforming in shape to said two flanges portions and disposed flat against the same in closed position, and further including a finger tab fixed to the outer end of said lever plate and extending about a plane transverse to that of said lever plate.

7. A syringe as claimed in claim 6, wherein the radially-outward edge of said notch relative to said pivot member is longer than the radially-inward edge 8. A syringe as claimed in claim 6, further including a downturned border, of L-shape section, depending from the outer end of said lever plate for releasable engagement under the other one of said flange portions when said abutment member is in closed position.

9. A syringe as defined in claim 4, further including a casing in which the elastic sleeve is enclosed, said casing having two end portions freely and slidably surrounding said piston rod and adapted to abut against said coil spring and against said lever plate when the latter is in closed position.

* * * * *